United States Patent
Eggleston et al.

(10) Patent No.: US 12,064,210 B2
(45) Date of Patent: Aug. 20, 2024

(54) APPARATUS FOR OPTICAL COHERENCE TOMOGRAPHY WITHIN INTEGRATED OPTOELECTRONIC CIRCUIT

(71) Applicant: Nokia Technologies Oy, Espoo (FI)

(72) Inventors: Michael Eggleston, Columbus, OH (US); Mark Earnshaw, Berkeley Heights, NJ (US)

(73) Assignee: Nokia Technologies Oy, Espoo (FI)

( * ) Notice: Subject to any disclaimer, the term of this patent is extended or adjusted under 35 U.S.C. 154(b) by 964 days.

(21) Appl. No.: 16/967,604

(22) PCT Filed: Feb. 25, 2019

(86) PCT No.: PCT/FI2019/050148
§ 371 (c)(1),
(2) Date: Aug. 5, 2020

(87) PCT Pub. No.: WO2019/162576
PCT Pub. Date: Aug. 29, 2019

(65) Prior Publication Data
US 2021/0085184 A1 Mar. 25, 2021

(30) Foreign Application Priority Data
Feb. 26, 2018 (EP) .................................... 18158601

(51) Int. Cl.
*A61B 5/00* (2006.01)
*G01B 9/02* (2022.01)
(Continued)

(52) U.S. Cl.
CPC .......... *A61B 5/0066* (2013.01); *A61B 5/6831* (2013.01); *G01B 9/02051* (2013.01);
(Continued)

(58) Field of Classification Search
CPC ............ G01B 9/02051; G01B 9/02091; A61B 5/0066
See application file for complete search history.

(56) References Cited

U.S. PATENT DOCUMENTS 9,366,885 B2  6/2016 Rubio Guivernau et al.
9,532,738 B2  1/2017 Delbeke et al.
(Continued)

FOREIGN PATENT DOCUMENTS

WO 2014/088650 A1 6/2014
WO 2017/097886 A1 6/2017

OTHER PUBLICATIONS

Van Leeuwen, Ton G., Akca, Imran B., Angelou, Nikolaos, Weiss, Nicolas, Hoekman, Marcel, Leinse, Arne and Heideman, Rene G.. "On-chip Mach-Zehnder interferometer for OCT systems" Advanced Optical Technologies, vol. 7, No. 1-2, 2018, pp. 103-106. https://doi.org/10.1515/aot-2017-0061.*

(Continued)

*Primary Examiner* — Rebecca C Bryant
(74) *Attorney, Agent, or Firm* — Harrington & Smith (57) ABSTRACT

Examples of the disclosure relate to an apparatus, an optical coherence tomography device, a wearable electronic device and method of forming an apparatus for optical coherence tomography. The apparatus comprises at least one layer of silicon dioxide and an integrated optoelectronic circuit. The integrated optoelectronic circuit comprises at least an interferometer configured for optical coherence tomography wherein the integrated optoelectronic circuit is formed within the at least one layer of silicon dioxide.

20 Claims, 5 Drawing Sheets

(51) Int. Cl.
*G01B 9/0209* (2022.01)
*G01B 9/02091* (2022.01)

(52) U.S. Cl.
CPC .......... *G01B 9/0209* (2013.01); *A61B 5/6823* (2013.01); *A61B 2562/0238* (2013.01); *A61B 2562/12* (2013.01)

(56) References Cited

U.S. PATENT DOCUMENTS

| | | | |
|---|---|---|---|
| 9,816,803 B2 | 11/2017 | Kulkarni | |
| 10,345,233 B2* | 7/2019 | Bennett | G01N 21/45 |
| 2005/0047702 A1 | 3/2005 | Parker et al. | |
| 2014/0125983 A1 | 5/2014 | Nitkowski et al. | |
| 2014/0376001 A1* | 12/2014 | Swanson | G01S 7/4817 356/479 |
| 2017/0017083 A1 | 1/2017 | Samec et al. | |

OTHER PUBLICATIONS

Mohammadhosseini, Hakimeh, "Optical chips are looking under your skin," International Year of Light 2015 Blog, Aug. 11, 2015, https://light2015blogdotorg.wordpress.com/2015/08/11/optical-chips-are-looking-under-your-skin/.*

Wijesinghe, Lee, Ravichandran, Han, Jeong, Han, Jung, Kim, Jeon, (2017). Optical coherence tomography-integrated, wearable (backpack-type), compact diagnostic imaging modality for in situ leaf quality assessment. Applied Optics. 56. D108. 10.1364/AO.56.00D108.*

Schneider et al., "Optical Coherence Tomography System Mass-Producible on a Silicon Photonic Chip", Optics Express, vol. 24, No. 2, Jan. 2016, pp. 1573-1586.

Heck, "Highly Integrated Optical Phased Arrays: Photonic Integrated Circuits for Optical Beam Shaping and Beam Steering", Nanophotonics, vol. 6, No. 1, 2016, 16 pages.

Akca et al., "Towards a Miniaturized Optical Coherence Tomography System", CLEO: Laser Science to Photonic Applications, 2011, 2 pages.

Wang et al., "Silicon Photonic Integrated Circuit Swept-Source Optical Coherence Tomography Receiver with Dual Polarization, Dual Balanced, in-phase and Quadrature Detection", Biomedical Optics Express, vol. 6, No. 7, Jun. 2015, pp. 2562-2574.

Yurtsever et al., "Photonic Integrated Mach-Zehnder Interferometer with an On-chip Reference Arm for Optical Coherence Tomography", Biomedical Optics Express, vol. 5, No. 4, Mar. 2014, pp. 1050-1061.

Extended European Search Report received for corresponding European Patent Application No. 18158601.7, dated Jun. 20, 2018, 10 pages.

Pintus et al., "Integrated TE and TM Optical Circulators on Ultra-low-loss Silicon Nitride Platform", Optics Express, vol. 21, No. 4, Feb. 2013, pp. 5041-5052.

Andrews et al., "Towards a Wearable Non-invasive Blood Glucose Monitoring Device", Journal of Physics: Conference Series, vol. 365, 2012, 5 pages.

International Search Report and Written Opinion received for corresponding Patent Cooperation Treaty Application No. PCT/FI2019/050148, dated Apr. 2, 2019, 13 pages.

Office action received for corresponding Indian Patent Application No. 202047040962, dated Jul. 6, 2021, 7 pages.

* cited by examiner

APPARATUS FOR OPTICAL COHERENCE TOMOGRAPHY WITHIN INTEGRATED OPTOELECTRONIC CIRCUIT

RELATED APPLICATION

This application claims priority to PCT Application No. PCT/FI2019/050148, filed on Feb. 25, 2019, which claims priority to European Application No. 18158601.7, filed on Feb. 26, 2018, each of which is incorporated herein by reference in its entirety.

TECHNOLOGICAL FIELD

Examples of the disclosure relate apparatus for optical coherence tomography. The apparatus could be used in wearable devices.

BACKGROUND

Optical coherence tomography enables cross sectional imaging of an object by detecting light reflected from internal structures within the object. Optical coherence tomography can be used to biological tissues of a subject such as a retina, teeth, skin or other suitable parts of a subject. Optical coherence tomography can therefore provide useful information that can be used to assist in diagnosis of medical conditions.

BRIEF SUMMARY

According to various, but not necessarily all, examples of the disclosure there is provided an apparatus comprising: at least one layer of silicon dioxide; and an integrated optoelectronic circuit comprising at least an interferometer configured for optical coherence tomography wherein the integrated optoelectronic circuit is formed within the at least one layer of silicon dioxide.

The interferometer may comprise an input light guide, a beam splitter, a sample line light guide, a delay line light guide and an output light guide. The interferometer may comprise at least one mirror configured to reflect light back into the delay line.

The integrated optoelectronic circuit may comprise at least one optical circulator.

The integrated optoelectronic circuit may comprise a detector configured to detect light from the interferometer. The detector may comprise at least one diode. The detector may comprise a balanced diode pair.

The at least one layer of silicon dioxide may be provided on a substrate.

The integrated optoelectronic circuit may have a largest dimension of less than 10 mm.

According to various, but not necessarily all, examples of the disclosure there is provided an optical coherence tomography device comprising an apparatus as described above and a light source.

The light source may comprise a coherent light source.

The light source may comprise a laser.

According to various, but not necessarily all, examples of the disclosure there is provided a wearable electronic device comprising an optical coherence tomography device as described above and means for attaching the optical coherence tomography device to a subject.

The means for attaching the optical coherence tomography device to a subject may comprise a strap.

According to various, but not necessarily all, examples of the disclosure there is provided a wearable electronic device comprising an optical coherence tomography device as described above and an attachment portion configured to attach the optical coherence tomography device to a subject.

According to various, but not necessarily all, examples of the disclosure there is provided a method comprising: providing at least one layer of silicon dioxide; and forming an integrated optoelectronic circuit comprising at least an interferometer configured for optical coherence tomography within the at least one layer of silicon dioxide.

BRIEF DESCRIPTION

For a better understanding of various examples that are useful for understanding the detailed description, reference will now be made by way of example only to the accompanying drawings in which.

DETAILED DESCRIPTION

Examples of the disclosure relate to an apparatus 101 for optical coherence topography. The apparatus 101 comprises an integrated optoelectronic circuit 105 comprising at least an interferometer 109 configured for optical coherence tomography. The integrated optoelectronic circuit 105 is formed within at least one layer 103 of silicon dioxide. The use of silicon dioxide to form the integrated optoelectronic circuit 105 enables the apparatus 101 to be made small enough to fit in devices such as wearable devices and also cause a sufficiently low level of backscattering so that the signal quality provided by the interferometer 109 is of a sufficient quality for optical coherence tomography.

Figure 1:
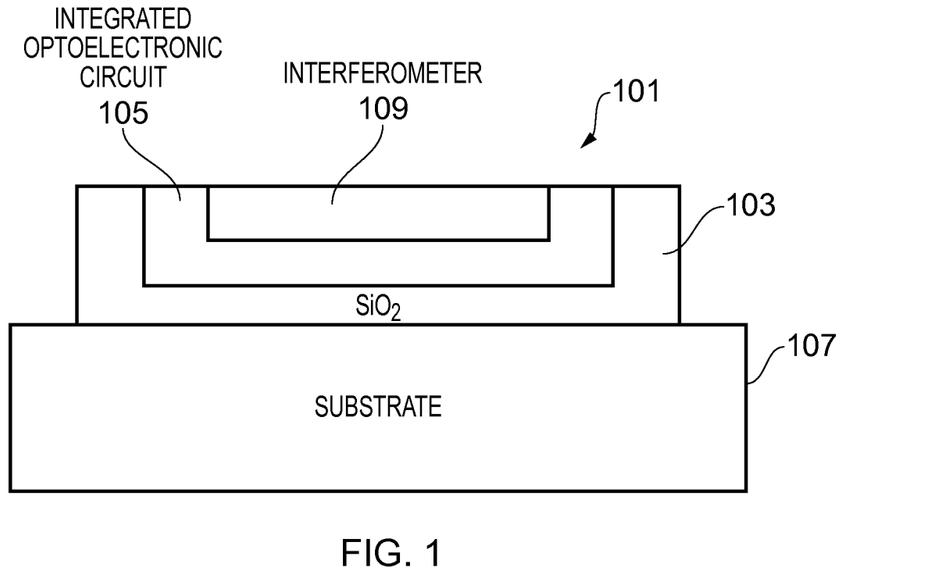
FIG. 1 illustrates an example apparatus.

FIG. 1 illustrates an example apparatus 101. The apparatus 101 comprises at least one layer 103 of silicon dioxide and an integrated optoelectronic circuit 105. In the example of FIG. 1 the apparatus 101 also comprises a substrate 107. It is to be appreciated that the apparatus 101 may comprise additional components that have not been shown in FIG. 1.

The substrate 107 may provide supporting means for the components of the apparatus 101. The supporting means could bear the weight, or at least partially, bear the weight of components of the apparatus 101. The components of the apparatus 101 may be mounted on the substrate 107. In some examples of the disclosure the substrate 107 does not provide any optical function in the operation of the apparatus 101.

The substrate 107 may comprise any suitable material. The substrate 107 may comprise a different material to the layer 103 of silicon dioxide. In some examples the substrate 107 may comprise silicon.

The at least one layer 103 of silicon dioxide is provided on the substrate 107. In the example of FIG. 1 one layer 103 of silicon dioxide is provided. Other numbers of layers 103 of silicon dioxide may be provided in other examples of the disclosure. In some examples the different layers 103 of silicon dioxide may have different levels of doping. The number of layers 103 of silicon dioxide that are provided may depend on the process that is used to fabricate the integrated optoelectronic circuit 105, the types of components within the integrated optoelectronic circuit 105 and/or any other suitable factors.

The layer 103 of silicon dioxide is thick enough to enable the integrated optoelectronic circuit 105 to be formed within the layer 103 of silicon dioxide. However the layer 103 of silicon dioxide is not too thick so that the apparatus 101 can be provided within a wearable device. In some examples the layer 103 of silicon dioxide may be 28 micrometres thick. In some examples the layer 103 of silicon dioxide could have a thickness of up to about 50 micrometres. In some examples the layer 103 of silicon dioxide could have a thickness between 8 micrometres and 50 micrometres.

The integrated optoelectronic circuit 105 is integrated within the layer 103 of silicon dioxide so that components of the integrated optoelectronic circuit 105 are formed from the silicon dioxide. The integrated optoelectronic circuit 105 may be formed from the silicon dioxide using any suitable fabrication methods. For instance, in some examples the integrated optoelectronic circuit 105 may be formed by providing a first layer of un-doped silicon dioxide on the substrate 107. In some examples the first layer of un-doped silicon dioxide may be deposited on the substrate 107. In other examples, where the substrate 107 is formed from silicon, the first layer of un-doped silicon dioxide may be formed by oxidising a part of the substrate 107. A second layer of doped silicon dioxide could then be deposited over the first layer. The doped layer of silicon dioxide may have a higher refractive index than the first layer of un-doped silicon dioxide. The doped layer of silicon dioxide can be patterned to form the optical waveguides of the integrated optoelectronic circuit 105. The doped layer of silicon dioxide can be patterned using photolithography and etching, ion exchange processes, and/or any other suitable processes. Once the pattern has been formed in the doped layer of silicon dioxide a further layer of doped silicon dioxide may be provided overlaying the pattern that has been formed. The further layer of silicon dioxide may have a higher refractive index than the first un-doped layer of silicon dioxide. It is to be appreciated that other methods of forming the integrated optoelectronic circuit 105 could be used in other examples of the disclosure.

Figure 2:
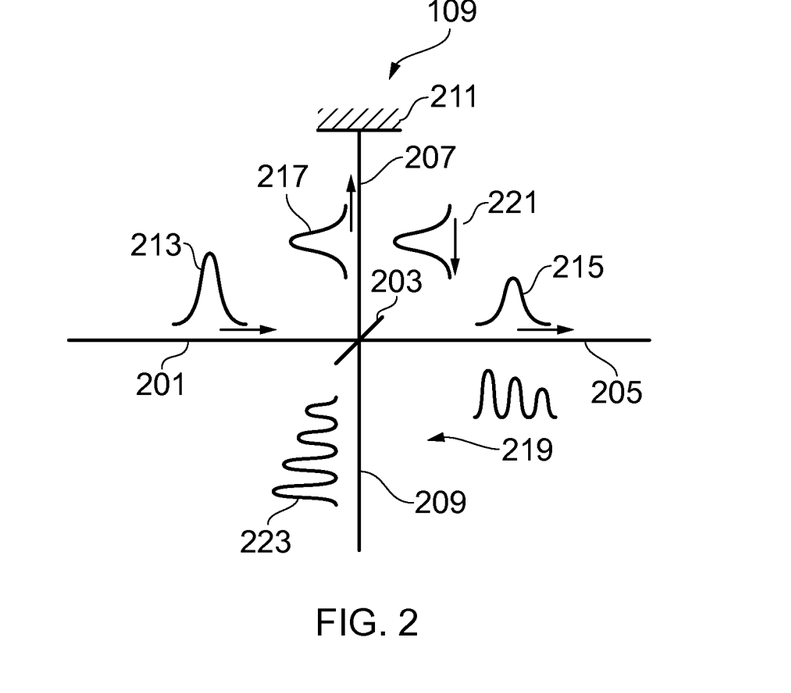
FIG. 2 illustrates an example interferometer according to examples of the disclosure.

In examples of the disclosure the integrated optoelectronic circuit 105 comprises an interferometer 109. The interferometer 109 is configured to enable optical coherence tomography. FIG. 2 illustrates an example of an interferometer 109 that may be used in some examples of the disclosure.

In some examples the integrated optoelectronic circuit 105 may comprise components in addition to the interferometer 109. For example the integrated optoelectronic circuit 105 may comprise at least one detector. The detector may be configured to detect light from the output light guide of the interferometer 109.

The detector may comprise any suitable means for detecting an input light signal and providing an output electrical signal in response to the detected input light signal. In some examples the detector may comprise one or more diodes. In some examples the detector may comprise a balanced diode pair. The type of detector that is used may depend upon the arrangement of the interferometer 109 that is used.

In some examples the integrated optoelectronic circuit 105 may comprise at least one optical circulator. The optical circulator may be configured to direct light that has been reflected from a sample towards the detector rather than back towards the light source. This may increase the sensitivity of the apparatus 101.

FIG. 2 schematically illustrates an interferometer 109 that may be used in examples of the disclosure. The components of the interferometer 109 may be formed within the layer 103 of silicon dioxide.

In the example of FIG. 2 the interferometer 109 comprises an input light guide 201, a beam splitter 203, a sample line light guide 205, a delay line light guide 207 and an output light guide 209. In the example of FIG. 2 the interferometer 109 also comprises a reflective mirror 211.

The input light guide 201 comprises means for receiving an input beam of light 213 and propagating the input beam of light 213 to the beam splitter 203. The input light guide 201 may be configured to be coupled to a light source. The light source may be provided separate to the interferometer 109 and/or the integrated optoelectronic circuit 105.

The beam splitter 203 is configured to the split the input beam of light 213 into two components. A first component beam of light 215 is directed down the sample line light guide 205 and a second component beam of light 217 is directed down the delay line light guide 207. In the example of FIG. 2 the beam splitter 203 is a 50/50 beam splitter so that the first component beam of light 215 and the second component beam of light 217 are equal. In other examples other types of the beam splitter may be used so that the component beams of light 215, 217 have different relative intensities.

The sample line light guide 205 comprises means for receiving the first component beam of light 215 and propagating the first component beam of light 215 to a sample. The sample is not shown in FIG. 2. The sample could comprise any suitable object. The sample could comprise biological tissue of a subject. In some examples the sample could comprise a subject's retina, teeth skin or any other suitable body part. The sample line light guide 205 is configured so that light reflected from the sample is propagated back towards the beam splitter 203 as a first reflected beam of light 219.

In the example interferometer 109 of FIG. 2 the delay line light guide 207 comprises means for receiving the second component beam of light 217 and propagating second component beam of light 217 to a reflective mirror 211. The delay line light guide 207 is configured so that light reflected from the reflective mirror 211 is propagated back towards the beam splitter 203 as a second reflected beam of light 221.

The first reflected beam of light 219 and the second reflected beam of light 221 combine to provide an output beam of light 223. The output light guide 209 is configured to propagate the output beam of light 223 out of the interferometer 109 and towards a detector. The detector may be provided separate to the interferometer 109 and/or the integrated optoelectronic circuit 105.

The electrical output of the detector comprises information about the light reflected from the sample. This can be processed to generate a three dimensional image of the sample.

In the example shown in FIG. 2 the interferometer 109 comprises a reflective mirror 211 configured to reflect light back into the delay line light guide 207 of the interferometer 109. In other examples the interferometer 109 need not comprise a mirror 211. For example the delay line light guide 207 could be provided directly towards the detector without any reflections.

In the examples of the disclosure the light guides 201, 205, 207, 209 within the interferometer 109 are formed from the layer 103 of silicon dioxide. As silicon dioxide has a low refractive index compared to materials such as silicon this reduces the amount of backscattering of light within the interferometer 109. This provides for a higher quality signal compared to light guides and interferometers 109 formed from silicon or other materials with a higher refractive index.

Figure 3A:
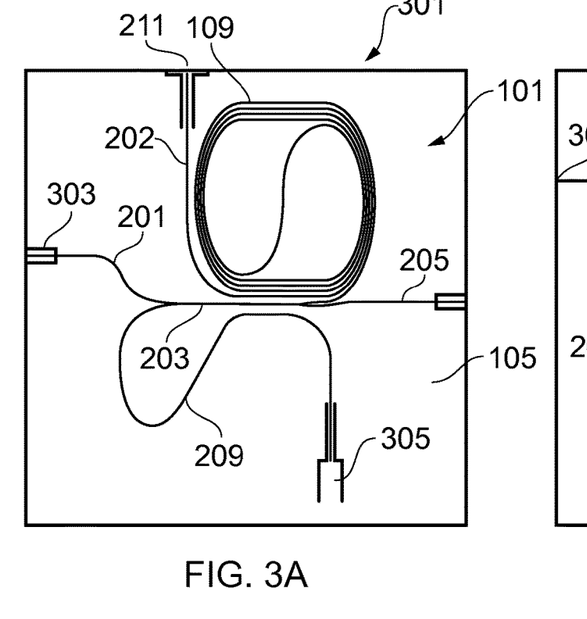
FIGS. 3A and 3B illustrate an optical coherence tomography device comprising an example apparatus.
Figure 3B:
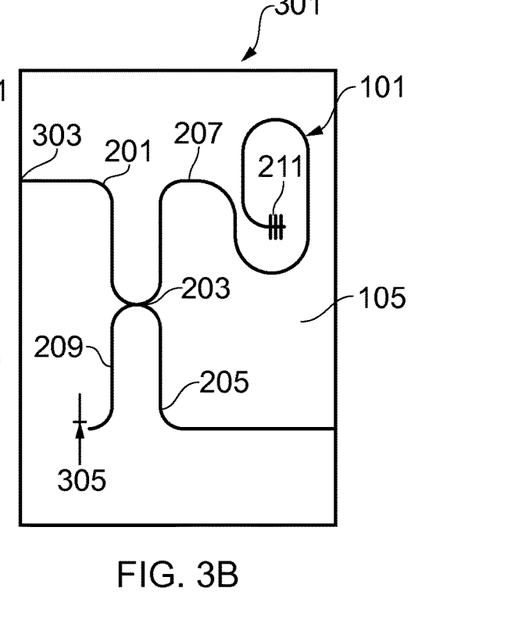

FIGS. 3A and 3B illustrate an optical coherence tomography device 301 according to examples of the disclosure. FIG. 3A illustrates an example layout of the components of the optical coherence tomography device 301. FIG. 3B schematically illustrates the example layout.

In the examples of FIGS. 3A and 3B the optical coherence tomography device 301 comprises an apparatus 101 and a light source 303. It is to be appreciated that other components may be provided within the optical coherence tomography device 301 in other examples of the disclosure.

The apparatus 101 used in the optical coherence tomography device 301 comprises an integrated optoelectronic circuit 105 comprising an interferometer 109. The interferometer 109 comprises an input light guide 201, a beam splitter 203, a sample line light guide 205, a delay line light guide 207 and an output light guide 209 which may be configured as described with reference to FIG. 2. In the example of FIGS. 3A and 3B the interferometer 109 also comprises a reflective mirror 211 configured to reflect light back into the delay line light guide 207.

In the example of FIGS. 3A and 3B the integrated optoelectronic circuit 105 also comprises a detector 305. The detector 305 may be positioned within the layer 103 of silicon dioxide. The detector 305 may be coupled to the output light guide 209 so that light from the output light guide 209 is incident on the detector 305.

In the examples of FIGS. 3A and 3B the detector 305 comprises a diode such as a photodiode. Other types of detector 305 may be used in other examples of the disclosure.

In the example of FIGS. 3A and 3B the optical coherence tomography device 301 also comprises a light source 303. The light source 303 may comprise a coherent light source such as a laser or any other suitable light source 303.

In the example of FIGS. 3A and 3B the light source 303 may be provided within the layer 103 of silicon dioxide. In other examples the light source 303 could be provided on a different chip or substrate 107.

Figures 4A, 4B:
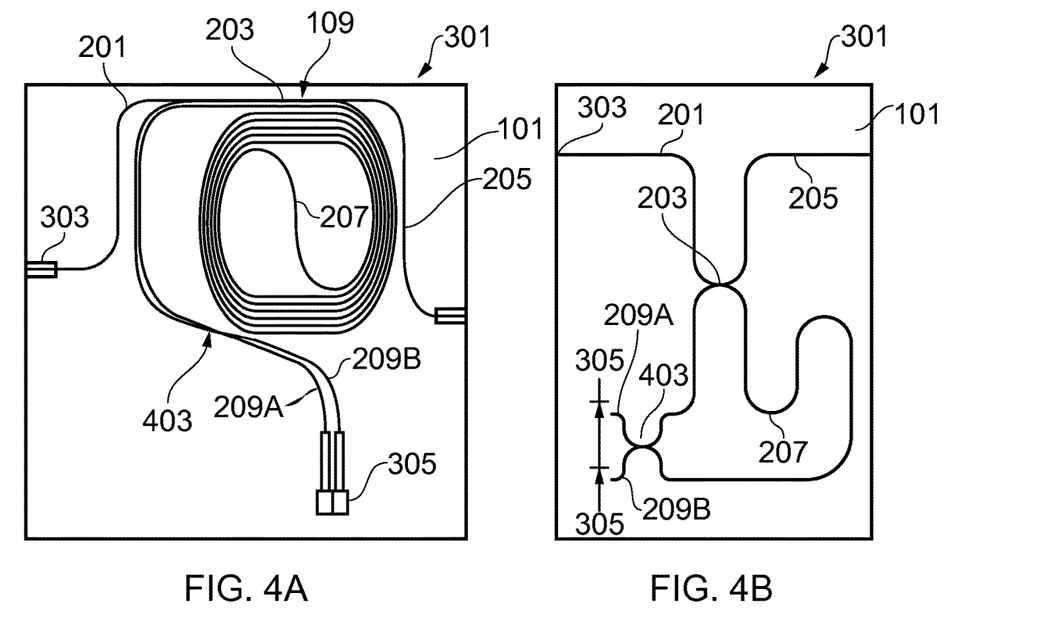
FIGS. 4A and 4B illustrate another optical coherence tomography device comprising an example apparatus.

FIGS. 4A and 4B illustrate another optical coherence tomography device 301 according to examples of the disclosure. FIG. 4A illustrates an example layout of the components of the optical coherence tomography device 301. FIG. 4B schematically illustrates the example layout.

In the examples of FIGS. 4A and 4B the optical coherence tomography device 301 comprises an apparatus 101 and a light source 303. It is to be appreciated that other components may be provided within the optical coherence tomography device 301 in other examples of the disclosure.

The apparatus 101 used in the optical coherence tomography device 301 comprises an integrated optoelectronic circuit 105 comprising an interferometer 109. The interferometer 109 comprises an input light guide 201, a first beam splitter 203, a sample line light guide 205, a delay line light guide 207, a second beam splitter 401 and two output light guides 209. The interferometer 109 used in the example optical coherence tomography device 301 of FIGS. 4A and 4B has a different layout to the example interferometer 109 used in the example optical coherence tomography device 301 of FIGS. 3A and 3B.

In the example of FIGS. 4A and 4B the input light guide 201 is configured to receive an input beam of light and propagate the input beam of light to the first beam splitter 203. The first beam splitter 203 is then configured to the split the input beam of light into two components so that a first component beam of light is directed down the sample line light guide 205 and a second component beam of light 217 is directed down the delay line light guide 207.

The sample line light guide 205 is configured to receive the first component beam of light and propagate the first component beam of light to a sample. The sample line light guide 205 is also configured so that light reflected from the sample is propagated back towards the first beam splitter 203.

In the example of FIGS. 4A and 4B the delay line light guide 207 is configured to receive the second component beam of light. In the example of FIGS. 4A and 4B the interferometer 109 does not comprise the reflective mirror 211. Instead the delay line light guide 207 is configured to propagate the second component of the beam of light to the second beam splitter 403.

At the second beam splitter 403 the light from the delay line is combined with light reflected back from the sample and split into two components so that a first output beam of light is directed down a first output light guide 209 and a second output beam of light is directed down a second output light guide 209.

The output beams of light are then incident on the detector 305. In the example of FIGS. 4A and 4B the detector 305 comprises a balanced diode pair. In other examples other types of detector 305 could be used.

In the example of FIGS. 4A and 4B the optical coherence tomography device 301 also comprises a light source 303. The light source 303 may comprise a coherent light source such as a laser or any other suitable light source 303.

In the example of FIGS. 4A and 4B the light source 303 may be provided within the layer 103 of silicon dioxide. In other examples the light source 303 could be provided on a different chip or substrate 107.

Figure 5:
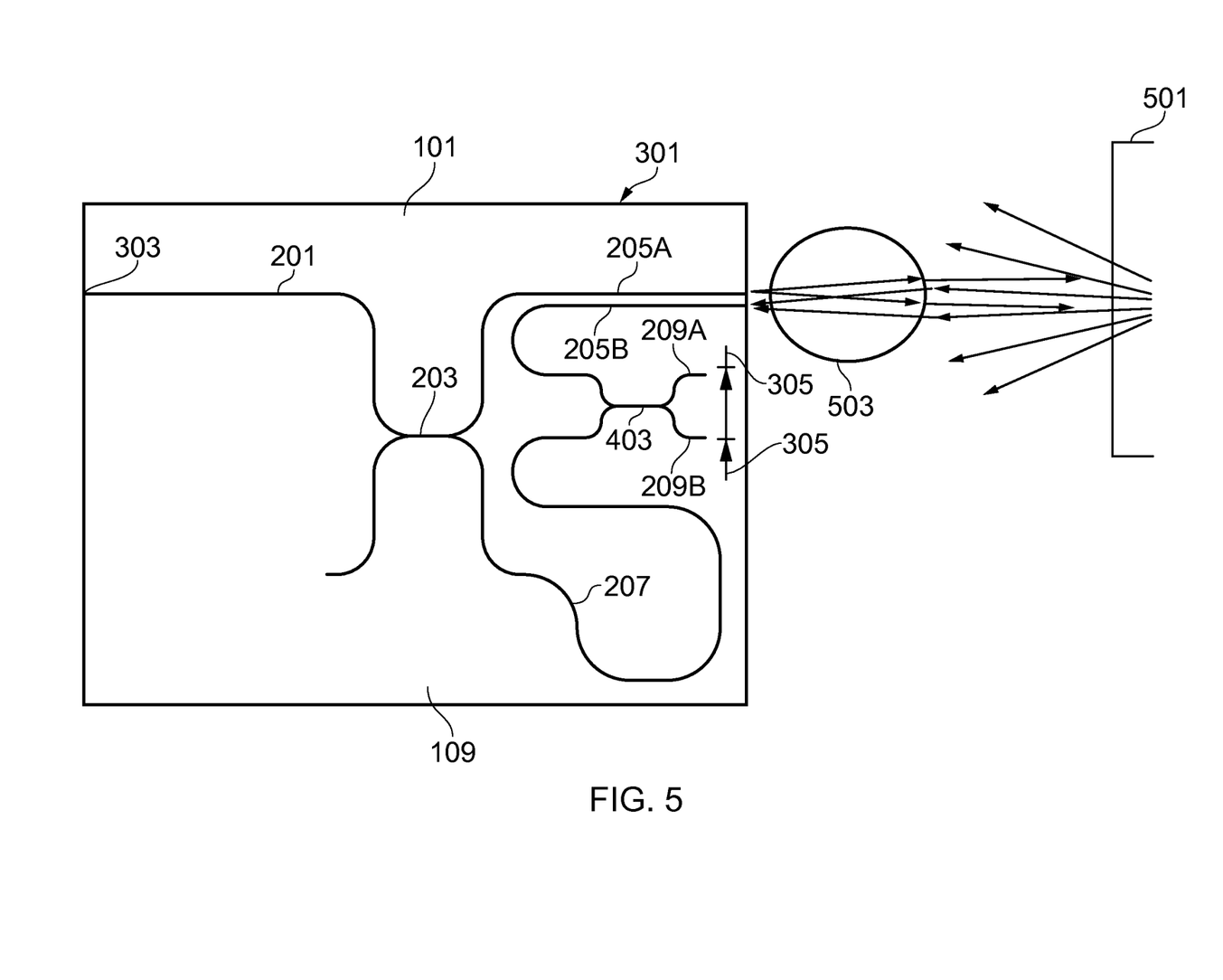
FIG. 5 illustrates another optical coherence tomography device comprising an example apparatus.

FIG. 5 illustrates another optical coherence tomography device 301 according to examples of the disclosure.

In the example of FIG. 5 the optical coherence tomography device 301 comprises an apparatus 101 and a light source 303. It is to be appreciated that other components may be provided within the optical coherence tomography device 301 in other examples of the disclosure. The optical coherence tomography device 301 is positioned adjacent to a sample 501. A free space coupler 503 is provided between the optical coherence tomography device 301 and the sample 501. The free space coupler 503 may be configured to collimate light directed from the optical coherence tomography device 301 towards the sample 501 and also to collimate light reflected back from the sample 501 into the optical coherence tomography device 301. The free space coupler 503 may comprise one or more lenses or any other suitable optical components.

As with the previously described examples, the apparatus 101 used in the optical coherence tomography device 301 in the example of FIG. 5 comprises an integrated optoelectronic circuit 105 comprising an interferometer 109. However in the example of FIG. 5 the interferometer 109 has a different lay out.

In the example interferometers 109 of FIGS. 3A to 4B a single sample line light guide 205 is provided. In these examples the single sample line light guide 205 propagates light towards a sample and propagates reflected light away from the sample. In the example of FIG. 5 the integrated optoelectronic circuits 105 comprises a plurality of sample line light guides 205. In the example of FIG. 5 two sample line light guides 205A, 205B are provided. In the example of FIG. 5 a first sample line light guide 205A is configured to propagate light towards the sample 501 and a second sample line light guide 205B is configured to propagate light away from the sample 501. The reflected light can then be mixed with the reference beam from the delay line light guide 207 of light and directed towards one or more photodetectors 305. In the example of FIG. 5 the light reflected from the sample 501 does not need to pass through the first beam splitter 203 which therefore reduces the losses in the optical signal.

It is to be appreciated that other configurations of the integrated optoelectronic circuit 105 could be used in other example optical coherence tomography devices 301. For instance, in the examples shown in FIGS. 3A to 5 the beam splitters 203, 403 are 50/50 beam splitters which split a beam of light into two component beams of equal intensities. In other examples the beam splitters 203, 403 might not be 50/50 beam splitters. For instance the first beam splitter 203 could be configured to send more light down the sample line light guide 205 than down the delay line light guide 207. How the beam splitter 203 is configured to divide light between the sample line light guide 205 and the delay line light guide 207 may dependent upon the optical properties of the sample. Where the sample has a high reflectivity more light may be provided in the delay line light guide 207 than in the sample line light guide 205 and where the sample has a low reflectivity more light may be provided in the sample line light guide 205 than in the delay line light guide 207.

In some examples one or more of the beam splitters 203, 403 could be tuneable beam splitters. The beam splitters 203, 403 could be tuneable via a thermo-optic effect or via any other suitable means. The tuneable beam splitters 203, 403 could be configured to be dynamically adjusted for different applications or different sample reflectivity.

In the example of FIGS. 4A to 5 the second beam splitter 403 may be configured so that equal amounts of light are provided between the two in diodes of the detector 305. Other arrangements of the second beam splitter 403 could be provided in other examples of the disclosure.

In some examples the integrated optoelectronic circuits 105 and/or the interferometers 109 may comprise means for adjusting the relative phases of the beams of light from the sample line light guides 205 and the delay line light guides 207. In some examples the means for adjusting the relative phases may be embedded within the interferometer 109 or within any suitable location in the integrated optoelectronic circuit 105. The means for adjusting the relative phases may comprise means for controlling the optical length of the delay line light guide 207 The means for adjusting the relative phases may comprise a phase shifter, a tuneable thermo-optic phase shifter or any other suitable means.

It is to be appreciated that other types of interferometer 109 could be used in examples of the disclosure. For instance, in some examples a Mach-Zehnder interferometer 109 could be used instead of the example interferometers described above. In such examples phase delays may be introduced by controlling the length of the delay line light guides within the Mach-Zehnder interferometer 109

Figure 6:
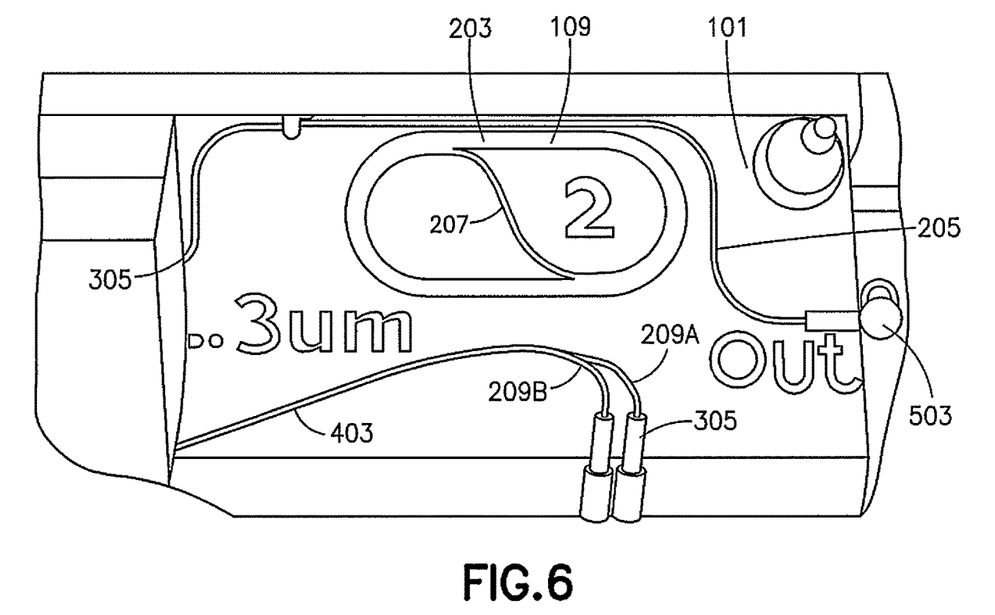
FIG. 6 is a photograph of an example optical coherence tomography device.

FIG. 6 is a photograph of an example optical coherence tomography device 301. The optical coherence tomography device 301 in FIG. 6 has a layout as shown in FIGS. 4A and 4B.

In the example of FIG. 6 the optical coherence tomography device 301 also comprises a free space coupler 503. The free space coupler 503 is positioned adjacent to the sample line light guide 205 and configured to direct light towards a sample. The sample is not shown in FIG. 6. The free space coupler 503 may be adjustable to enable the beam of light from the interferometer to be moved relative to the sample. In some examples the free space coupler 503 may enable the beam of light to be moved in two dimensions. This may enable a three dimensional image to be obtained by the optical coherence tomography device 301.

In the examples of FIGS. 3A to 6 the example integrated optoelectronic circuit 105 has a largest dimension of 10 mm or less. In the example of FIGS. 3A to 6 the example integrated electronic circuit 105 has a length of 10 mm or less and a width of 5 mm or less. Other sizes of the integrated optoelectronic circuit 105 could be used in other examples of the disclosure. The size of the integrated optoelectronic circuit 105 may be such that it enables the optical coherence tomography device 301 to be provided within a wearable device 601.

Figure 7:
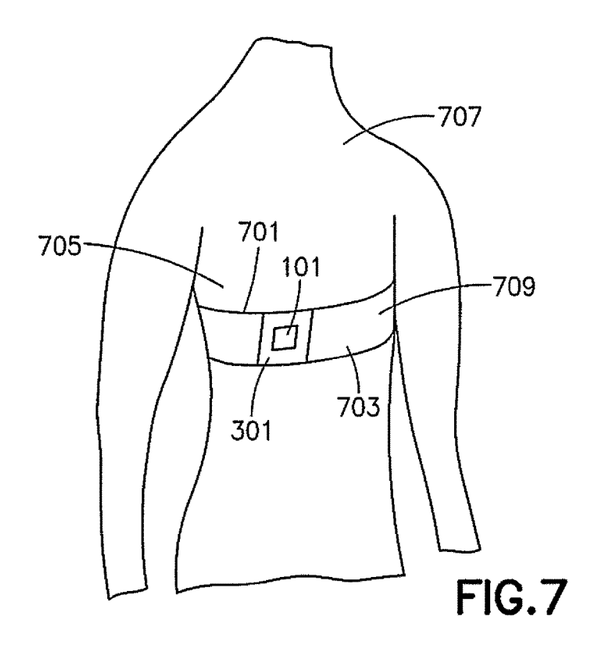
FIG. 7 illustrates an example wearable electronic device.

FIG. 7 illustrates an example wearable electronic device 701 according to examples of the disclosure. The wearable electronic device 701 comprises an optical coherence tomography device 301 and means 703 for attaching the optical coherence tomography device 301 to a subject. In the example of FIG. 7 the wearable electronic device 701 is shown attached to the torso 705 of a subject 707.

The optical coherence tomography device 301 which is used within the wearable electronic device 701 may be as described above or may be any other suitable optical coherence tomography device 301. For example, the optical coherence tomography device 301 could be any of the optical coherence tomography devices 301 shown in FIGS. 3A to 6 or a different optical coherence tomography device 301.

The means 703 for attaching the optical coherence tomography device 301 to a subject 707 may comprise any means which enables the optical coherence tomography device 301 to be secured to the body of a subject 707 so that the optical coherence tomography device 301 can obtain images of a part of the body of the subject 707.

In the example of FIG. 7 the means 703 for attaching the optical coherence tomography device 301 to a subject 707 comprises a strap 709. The strap 709 may be sized and shaped to fit around any suitable part of the subject 707. In the example of FIG. 7 the strap 709 is configured to fit around the torso 705 of the subject 707. This may enable the subject's chest or other part of their torso 705 to be analysed using the optical coherence tomography device 301.

In other examples the strap 709 could be sized and shaped to fit around a different part of the subject 707. For instance, in some examples the strap 709 could be sized and shaped to fit around the subject's arm. In such examples the optical coherence tomography device 301 could be integrated within a watch or other wrist mounted device.

In other examples the optical coherence tomography device 301 could be configured to obtain images of a subject's retina or other part of their eye. In such examples the optical coherence tomography device 301 could be integrated within a head mounted device or any other suitable wearable device.

In other examples the wearable electronic device 701 and the optical coherence tomography device 301 could be configured to be attached to a different part of a subject. For example the wearable electronic device 701 and the optical coherence tomography device 301 could be configured to fit to a subject's finger, ear lobe or any other suitable part of their body.

In the example of FIG. 7 the wearable electronic device 701 comprises a single optical coherence tomography device 301. In other examples the wearable electronic device could comprise a plurality of optical coherence tomography devices 301. In such examples the wearable electronic device 701 may be configured so that different optical coherence tomography devices 301 can obtain images of different parts of the subject.

Figure 8:
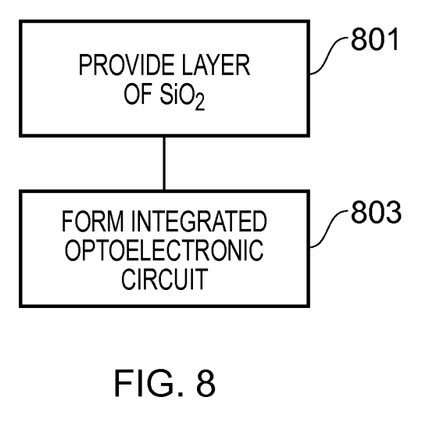
FIG. 8 illustrates an example method of forming an apparatus.

FIG. 8 illustrates an example method of forming an apparatus 101. The method may be used to form an apparatus 101 which may be as described above.

The method comprises, at block 801, providing at least one layer 103 of silicon dioxide. The at least one layer 103 of silicon dioxide may be provided on a substrate 107. In some examples providing the at least one layer 103 of silicon dioxide may comprise forming the at least one layer 103 of silicon dioxide on the substrate 107.

The method also comprises, at block 803, forming an integrated optoelectronic circuit 105 within the at least one layer 103 of silicon dioxide. The integrated optoelectronic circuit 105 comprises an interferometer 109 configured for optical coherence tomography.

It is to be appreciated that in some examples the method may comprise additional blocks that are not shown in FIG. 8. For example the method could comprise providing one or more mirrors within the interferometer 109.

Once the apparatus 101 has been formed the apparatus 101 may be coupled to one or more additional components to provide an optical coherence tomography device 301. For example, the method could comprise additional blocks of coupling the apparatus 101 to a light source 303 such as a laser. The light source could be provided on the substrate 107 or in any other suitable position.

Once the optical coherence tomography device 301 has been formed the optical coherence tomography device 301 may be coupled to one or more additional components to provide a wearable electronic device 601. For example the optical coherence tomography device 301 may be secured to a strap 609 or other attachment means 603 to enable the optical coherence tomography device 301 to be worn by a subject.

Examples of the disclosure provide for an apparatus 101 that can be used within optical coherence tomography devices 301. The apparatus 101 is small enough to be used within wearable electronic devices 701. However as the interferometer 109 is formed within the layer 103 of silicon dioxide this provides a low level of backscatter and so enable a sufficiently high signal quality to be provided even with the small sized device.

As the optical coherence tomography device 301 can be provided within a wearable electronic device 701 this may enable the optical coherence tomography device 301 to be used to obtain information about the subject at different times and/or over an extended time period. The extended time period could be hours, days, weeks or even longer.

In this description the term "coupled" means operationally coupled. Any number of intervening components may be provided between coupled components, including zero components.

The term "comprise" is used in this document with an inclusive not an exclusive meaning. That is any reference to X comprising Y indicates that X may comprise only one Y or may comprise more than one Y. If it is intended to use "comprise" with an exclusive meaning then it will be made clear in the context by referring to "comprising only one . . . " or by using "consisting".

In this brief description, reference has been made to various examples. The description of features or functions in relation to an example indicates that those features or functions are present in that example. The use of the term "example" or "for example" or "may" in the text denotes, whether explicitly stated or not, that such features or functions are present in at least the described example, whether described as an example or not, and that they can be, but are not necessarily, present in some of or all other examples. Thus "example", "for example" or "may" refers to a particular instance in a class of examples. A property of the instance can be a property of only that instance or a property of the class or a property of a sub-class of the class that includes some but not all of the instances in the class. It is therefore implicitly disclosed that a feature described with reference to one example but not with reference to another example, can where possible be used in that other example but does not necessarily have to be used in that other example.

Although embodiments of the present invention have been described in the preceding paragraphs with reference to various examples, it should be appreciated that modifications to the examples given can be made without departing from the scope of the invention as claimed.

Features described in the preceding description may be used in combinations other than the combinations explicitly described.

Although functions have been described with reference to certain features, those functions may be performable by other features whether described or not.

Although features have been described with reference to certain embodiments, those features may also be present in other embodiments whether described or not.

Whilst endeavoring in the foregoing specification to draw attention to those features of the invention believed to be of particular importance it should be understood that the Applicant claims protection in respect of any patentable feature or combination of features hereinbefore referred to and/or shown in the drawings whether or not particular emphasis has been placed thereon.

The invention claimed is:

1. An apparatus comprising:
   at least one layer of silicon dioxide; and
   an integrated optoelectronic circuit comprising at least an interferometer configured for optical coherence tomography wherein the integrated optoelectronic circuit is formed within defining surfaces of the at least one layer of silicon dioxide such that at least a portion of the integrated optoelectronic circuit is formed from the at least one layer of silicon dioxide.

2. An apparatus as claimed in claim 1 wherein the interferometer comprises an input light guide, a beam splitter, a sample line light guide, a delay line light guide and an output light guide.

3. An apparatus as claimed in claim 2 wherein the interferometer comprises at least one mirror configured to reflect light back into the delay line.

4. An apparatus as claimed in claim 1 wherein the integrated optoelectronic circuit comprises at least one optical circulator.

5. An apparatus as claimed in claim 1 wherein the integrated optoelectronic circuit comprises a detector configured to detect light from the interferometer.

6. An apparatus as claimed in claim 5 wherein the detector comprises at least one diode.

7. An apparatus as claimed in claim 5 wherein the detector comprises a balanced diode pair.

8. An apparatus as claimed in claim 1 wherein the at least one layer of silicon dioxide is provided on a substrate.

9. An apparatus as claimed in claim 1 wherein the integrated optoelectronic circuit has a largest dimension of less than 10 mm.

10. An apparatus as claimed in claim 1, wherein the integrated optoelectronic circuit comprises a detector configured to detect light from the interferometer; the at least one layer of silicon dioxide is provided on a substrate; and the apparatus comprises a light source located on the substrate.

11. An apparatus as claimed in claim 1 wherein the apparatus further comprises a coherent light source.

12. An apparatus as claimed in claim 11 wherein the light source comprises a laser.

13. A method comprising:
providing at least one layer of silicon dioxide; and
forming an integrated optoelectronic circuit comprising at least an interferometer configured for optical coherence tomography within defining surfaces of the at least one layer of silicon dioxide such that at least a portion of the integrated optoelectronic circuit is formed from the at least one layer of silicon dioxide.

14. A wearable electronic device comprising:
optical coherence tomography device comprising a light source; at least one layer of silicon dioxide; and an integrated optoelectronic circuit comprising at least an interferometer configured for optical coherence tomography wherein the integrated optoelectronic circuit is formed within defining surfaces of the at least one layer of silicon dioxide such that at least a portion of the integrated optoelectronic circuit is formed from the at least one layer of silicon dioxide; and
attachment configured to attach the optical coherence tomography device to a subject.

15. A wearable electronic device as claimed in claim 14 wherein the attachment configured to attach the optical coherence tomography device to a subject comprises a strap.

16. A wearable electronic device as claimed in claim 4 wherein the interferometer comprises an input light guide, a beam splitter, a sample line light guide, a delay line light guide and an output light guide.

17. A wearable electronic device as claimed in claim 16 wherein the interferometer comprises at least one mirror configured to reflect light back into the delay line.

18. A wearable electronic device as claimed in claim 14 wherein the integrated optoelectronic circuit comprises at least one optical circulator.

19. A wearable electronic device as claimed in claim 14 wherein the integrated optoelectronic circuit comprises a detector configured to detect light from the interferometer.

20. A wearable electronic device as claimed in claim 19 wherein the detector comprises at least one diode.

* * * * *